(12) United States Patent
Yaroshenko et al.

(10) Patent No.: US 11,980,494 B2
(45) Date of Patent: May 14, 2024

(54) SYSTEM, METHOD AND COMPUTER PROGRAM FOR ACQUIRING PHASE IMAGING DATA OF AN OBJECT

(71) Applicant: KONINKLIJKE PHILIPS N.V., Eindhoven (NL)

(72) Inventors: Andriy Yaroshenko, Hamburg (DE); Thomas Koehler, Norderstedt (DE); Hanns-Ingo Maack, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 348 days.

(21) Appl. No.: 17/431,559

(22) PCT Filed: Feb. 10, 2020

(86) PCT No.: PCT/EP2020/053339
§ 371 (c)(1),
(2) Date: Aug. 17, 2021

(87) PCT Pub. No.: WO2020/173695
PCT Pub. Date: Sep. 3, 2020

(65) Prior Publication Data
US 2022/0133257 A1 May 5, 2022

(30) Foreign Application Priority Data
Feb. 28, 2019 (EP) ..................... 19159860

(51) Int. Cl.
A61B 6/00 (2006.01)
A61B 6/42 (2024.01)
G01N 23/041 (2018.01)

(52) U.S. Cl.
CPC ............ A61B 6/542 (2013.01); A61B 6/4291 (2013.01); A61B 6/484 (2013.01); A61B 6/545 (2013.01);
(Continued)

(58) Field of Classification Search
CPC ....... A61B 6/542; A61B 6/4291; A61B 6/484; A61B 6/545; A61B 6/4035; G01N 23/041; G21K 2207/005
See application file for complete search history.

(56) References Cited

U.S. PATENT DOCUMENTS

2012/0140893 A1* 6/2012 Feuerlein ............... A61B 6/542
378/108
2012/0145912 A1* 6/2012 Iwakiri ................. A61B 6/484
250/336.1
(Continued)

FOREIGN PATENT DOCUMENTS

CN 104367331 A 2/2015
JP 2004173892 A 6/2004
(Continued)

OTHER PUBLICATIONS

PCT International Search Report, International application No. PCT/EP2020/053339, dated Mar. 25, 2020.
(Continued)

Primary Examiner — Christine S. Kim
(74) Attorney, Agent, or Firm — Larry Liberchuk

(57) ABSTRACT

The invention relates to a control module for controlling an x-ray system (140) during the acquisition of step images for phase imaging. The control module comprises a step image quantity providing unit (111) for providing a step image quantity, a detector dose providing unit (112) for providing a target detector dose, an applied detector dose determination unit (113) for determining an applied detector dose absorbed by a part of the detector (144) during the acquisition of a step image, and a step image acquisition control unit (114) for controlling the x-ray imaging system (140) during the acquisition of each step image based on the applied detector dose, the target detector dose and the step image quantity. The control module allows to control the
(Continued)

x-ray imaging system such that the target detector dose is not exceeded while at the same time ensuring a sufficient quality of the step images.

15 Claims, 3 Drawing Sheets

(52) U.S. Cl.
CPC ..... *G01N 23/041* (2018.02); *G21K 2207/005* (2013.01)

(56) References Cited

U.S. PATENT DOCUMENTS

| 2014/0146945 A1 | 5/2014 | Fredenberg |
| 2015/0362444 A1 | 12/2015 | Nagai |
| 2017/0343494 A1 | 11/2017 | Hoshino |

FOREIGN PATENT DOCUMENTS

| JP | 2004209152 A | 7/2007 | |
| JP | 2008079923 A | 4/2008 | |
| JP | 2014012030 A | 1/2014 | |
| WO | WO2012057278 A1 | 3/2012 | |
| WO | WO-2017093055 A1 * | 6/2017 | ........... A61B 6/4035 |
| WO | WO2017093055 A1 | 6/2017 | |

OTHER PUBLICATIONS

Weitkamp, T. et al., "X-Ray Phase Imaging With a Grating Interferometer", Optics Express, 13.16 (2005): 6296-6304.
Pfeiffer, F. et al., "Hard-X-ray Dark-Field Imaging Using a Grating Interferometer", Nature Materials, vol. 7, pp. 134 to 137, 2008.
Koehler, T. et al., "Slit-Scanning Differential X-Ray Phase-Contrast Mammography: Proof-of-Concept Experimental Studies", Medical Physics, vol. 42, issue 4, pp. 1959 to 1965, Apr. 2015.

* cited by examiner

SYSTEM, METHOD AND COMPUTER PROGRAM FOR ACQUIRING PHASE IMAGING DATA OF AN OBJECT

FIELD OF THE INVENTION

The invention relates to a control module, a method and a computer program for acquiring phase imaging data of an object.

BACKGROUND OF THE INVENTION

In x-ray imaging applications it is important to accurately control an x-ray radiation dose applied to an object, since an excessive dose of x-ray radiation might be harmful for the object, whereas a too low x-ray dose can lead to a reduced image quality. In standard x-ray imaging, an Automatic Exposure Control (AEC) is used to ensure that the correct radiation dose is provided, wherein the AEC automatically switches a radiation source off if a predetermined radiation dose is reached on the detector. Today, in addition to standard x-ray imaging, x-ray phase imaging, which results, for instance, in dark-field and phase-contrast images, becomes more widely used. In x-ray phase imaging applications, often a plurality of x-ray images has to be acquired during acquisition of phase imaging data. Presently, it is not possible to also apply an AEC to the acquisition of such x-ray phase imaging data and therefore an x-ray dose provided to an imaged object cannot be accurately controlled in these applications.

SUMMARY OF THE INVENTION

It is an object of the present invention to provide a control module, a method and a computer program that allow for accurately controlling a radiation dose applied to an object during the acquisition of phase imaging data.

In a first aspect of the invention a control module for controlling an x-ray imaging system during the acquisition of phase imaging data of an object using phase stepping is presented, wherein during the phase stepping a plurality of step images, each with a different phase of an interference pattern relative to the object, is acquired with an x-ray imaging system, wherein the phase imaging data comprises the step images, wherein the control module comprises a) a step image quantity providing unit for providing a step image quantity referring to a number of step images that are planned to be acquired during the phase stepping for acquiring the phase imaging data, b) a detector dose providing unit for providing a target detector dose, wherein the target detector dose corresponds to a radiation dose absorbed by at least a part of the detector during the acquisition of the phase imaging data that should not be exceeded, c) an applied detector dose determination unit for determining an applied detector dose indicative of a radiation dose absorbed by at least the part of the detector during the acquisition of a step image, d) a step image acquisition control unit for controlling the x-ray imaging system during the acquisition of each step image based on the applied detector dose, the target detector dose and the step image quantity, wherein the controlling comprises controlling acquisition parameters that each step image is acquired with.

Since the control module is adapted to control the x-ray imaging system during the acquisition of the phase imaging data and in particular is adapted to control the x-ray imaging system during the acquisition of each step image based on the applied detector dose, the target detector dose and the step image quantity, the radiation dose received by the object during the acquisition of the phase imaging data can be accurately controlled. In particular, the x-ray imaging system can be controlled such that the target detector dose is not exceeded while at the same time providing the necessary radiation to ensure a sufficient quality of the step images.

The control module is adapted to control an x-ray imaging system during the acquisition of phase imaging data of an object. The object can be, for instance, a living being, like an animal or a human patient, or can be an inanimate object, like a suitcase. Preferably, the object is a patient and the phase imaging data is acquired in a medical context. Phase imaging is used to acquire information on changes in a phase of a radiation beam passing through the object. This information can be provided to a user, for instance, by transforming the phase shift of the radiation beam into intensity variations in an image. However, the phase information can also be provided to a user in other forms, for instance, by reconstructing a dark-field image from the phase information. Phase imaging data refers to data that is acquired during x-ray phase imaging and can be, for instance, used for reconstructing an image like a phase-contrast image, an attenuation image, and/or a dark-field image.

The x-ray imaging system controlled by the control module is adapted to acquire phase imaging data using phase stepping. A standard system for acquiring phase imaging data using phase stepping comprises a radiation source and a detector for detecting the radiation of the radiation source after it has passed through the object. Further such an x-ray imaging system comprises at least two gratings that can be moved relative to each other. During phase imaging with such a standard system the gratings are used to generate an interference pattern. By moving the gratings relative to each other, the phase of the interference pattern relative to the object can be changed. From images acquired with different positions of the gratings, phase imaging data corresponding to phase information of the radiation having passed the object can be extracted and phase-contrast, attenuation, and/or dark-field images can be reconstructed. The same effect can be achieved with an alternative x-ray imaging system, wherein for providing the phase stepping, a source spot of the radiation source is moved. This kind of phase stepping is also known as electromagnetic phase stepping. Accordingly, an x-ray imaging system for acquiring phase imaging data using phase stepping is adapted to provide at least one possibility to acquire a plurality of step images, wherein the step images are acquired each with a different phase of an interference pattern relative to the object.

The control module is adapted to control the acquisition of each step image during the phase stepping. The control module can be provided as part of the x-ray imaging system or can be provided as external stand-alone system, for instance, on a computer system, that is connected with the x-ray imaging system for controlling the x-ray imaging system.

The control module comprises the step image quantity providing unit that is adapted to provide a step image quantity. The step image quantity providing unit can be a storing unit on which the step image quantity is stored already and from which the step image quantity can be retrieved. Also, the step image quantity providing unit can be a retrieving unit for retrieving the step image quantity from, for instance, an input device into which a user inputs the step image quantity, wherein the step image quantity providing unit is then adapted to provide the received step image quantity. The step image quantity refers to the planned quantity of step images that should be acquired during the phase stepping. Moreover, the step image quantity also defines the quantity of different positions that a grating or source spot adopts during the acquisition of the phase imaging data. Thus, each step image corresponds to a different position of the grating or source spot. It is preferred that for the acquisition of phase imaging data the provided step image quantity lies between 5 and 10. However, also a lower step image quantity, for instance, 3, or a higher step image quantity, for instance, 15, can be provided. Preferably, the step image quantity is at least 3 such that at least 3 step images at three different positions of a grating or source spot are acquired.

Further, the control module comprises a detector dose providing unit that is adapted to provide a target detector dose. Also, the detector dose providing unit can be a storing unit in which the target detector dose is stored already and from which the target detector dose can be retrieved. The detector dose providing unit can also be a retrieving unit for retrieving the target detector dose, for instance, from an input unit to which the user provides a desired target detector dose, wherein the detector dose providing unit is then adapted to provide the received target detector dose. The target detector dose corresponds to a maximum radiation energy absorbed by at least a part of the detector during the acquisition of the phase imaging data, wherein the target detector dose should not be exceeded. The target detector dose can be provided with respect to the whole detector or with respect to only a specific part of the detector. For instance, a user can indicate a region in an image of an object as a region of interest of the object, wherein the detector dose providing unit is then adapted to estimate which parts of the detector correspond to the region in the image indicated by the user. For instance, the detector dose providing unit can be adapted to estimate where the region indicated by the user is positioned with respect to the object and can then estimate or be provided with a position of the object relative to the detector. Alternatively, the detector dose providing unit can be adapted to automatically provide a part of the detector for which the target detector dose should not be exceeded, for instance, based on a known general position of the object or based on an expected radiation pattern on the detector.

The part of the detector for which the target detector dose should not be exceeded can correspond, for instance, to a structure within the object. Preferably, the part of the detector corresponds to a specific organ of a patient like a lung or a heart or to another anatomical structure. Preferably, the target detector dose refers to an average radiation dose that should not be exceeded on average in the determined part of the detector. Alternatively, the target detector dose can also correspond to a maximum radiation dose that should not be exceeded anywhere in the determined part of the detector. Preferably, the target detector dose is provided as an overall radiation dose, i.e. the radiation dose acquired by the detector after the complete acquisition of the phase imaging data.

The control module further comprises an applied detector dose determination unit that is adapted to determine an applied detector dose. The applied detector dose determination unit can also be an applied detector dose measurement unit that directly measures the applied detector dose, for instance, through a radiation sensor. Preferably, the applied detector dose determination unit is adapted to determine the applied detector dose based on the signals provided by the radiation detector. The applied detector dose, preferably, corresponds to a radiation dose that is absorbed by the at least a part of the detector during the acquisition of a step image. Preferably, the applied detector dose determination unit is adapted to determine the applied detector dose in real-time, i.e. integrating the radiation energy received by the detector continuously to acquire a currently already applied detector dose. Moreover, after the acquisition of a step image has been completed, the applied detector dose is indicative of an overall applied detector dose of the step image, preferably, corresponds to the radiation dose received by the detector during the complete acquisition of the step image. The applied detector dose determination unit can provide a storage unit or can be connected to a storage unit for storing the applied detector dose for each acquired step image. Preferably, the applied detector dose determination unit is adapted to determine the applied detector dose by calculating a histogram of the acquired step image and to determine the applied detector dose based on the histogram. For instance, an average value of the histogram is determined as the applied detector dose. Alternatively, first the acquired step image can be segmented and the areas comprising an object can be determined. Then the histogram is calculated for the parts of the step image that do not correspond to an object and the radiation value corresponding to, for instance, the $50^{th}$ percentile or the $80^{th}$ percentile is calculated and set as the applied detector dose. Further, the applied detector dose determination unit can be adapted to directly determine the detector dose applied to the detector, for instance, based on the currently provided radiation values of the detector elements.

Further, the control module comprises the step image acquisition control unit that is adapted to control the x-ray imaging system during the acquisition of each step image. The controlling comprises the controlling of acquisition parameters, for instance, an acquisition time, a tube current, a voltage applied to the radiation source, etc., during the acquisition of each step image. Preferably, the controlling comprises controlling as acquisition parameters a tube current and an acquisition time for each acquired step image. The step image acquisition control unit is adapted to control the acquisition of each step image based on the applied detector dose, the target detector dose and the step image quantity. For instance, the step image acquisition control unit can be adapted to control a tube current and/or an acquisition time of a step image such that the applied detector dose corresponds to a radiation dose necessary for acquiring an image with a sufficient image quality. Moreover, the image acquisition control unit can be adapted to control the acquisition of each step image such that it is ensured that all step images can be acquired with sufficient image quality, while at the same time ensuring that the target detector dose is not exceeded. Further, the step image acquisition control unit can also be adapted to terminate the acquisition of the phase imaging data if the applied detector doses of already acquired step images indicates that the target detector dose could be exceeded during the acquisition of the planned subsequent step images. Accordingly, the control module ensures accurate controlling of a radiation dose provided to the object.

In an embodiment, the detector dose providing unit is adapted to further provide a step dose for each step image, wherein the step dose is indicative for a radiation dose that is planned to be absorbed by at least the part of the detector during the acquisition of the respective step image, wherein the step image acquisition control unit is adapted to control the acquisition of each step image further based on the step dose. Preferably, the step dose corresponds to a radiation dose that is planned to be absorbed by at least the part of the detector during the acquisition of the respective step image. The step doses can, for instance, be determined by a user before the start of the acquisition of the phase imaging data and stored such that the detector dose providing unit can provide the step doses during the acquisition of the phase imaging data. The step dose can be the same for all step images or can be different for at least some of the step images. Preferably, the detector dose providing unit is adapted to provide the step dose based on the step image quantity and the target detector dose. For instance, the detector dose providing unit can be adapted to provide the step dose for each step image based on different already stored step doses assigned to a step image quantity and detector dose, wherein the detector dose providing unit then selects the step doses based on the step image quantity and the target detector dose for the current acquisition of phase imaging data. Preferably, the detector dose providing unit is adapted to determine the step doses based on the step image quantity and the detector dose. Even more preferably, the detector dose providing unit is adapted to determine a step dose for each step image such that it corresponds to a fraction of the target step dose calculated by dividing the target step dose by the step image quantity. The step image acquisition control unit is then adapted to control the acquisition of each step image further based on the step dose.

In an embodiment, the step image acquisition control unit is adapted to control the acquisition of a step image such that the acquisition is terminated when the applied detector dose reaches the step dose of the step image during the acquisition of the step image. The step image acquisition control unit can then be adapted to continue the acquisition of the phase imaging data with the next step image. Thus, it can be assured that the planned step dose for each step image is not exceeded.

In an embodiment, the step image quantity providing unit is further adapted to provide a planned acquisition time referring to a time that should not be exceeded by the acquisition of a step image, wherein the control unit is adapted to control the acquisition of the step images such that the acquisition of a step image is terminated either when the planned acquisition time is reached or the applied detector dose reaches the step dose of the step image during the acquisition of the step image. The step image acquisition control unit can then be adapted to continue the acquisition of the phase imaging data with the next step image. The planned acquisition time is preferably provided for applications in which fluoroscopic imaging data should be acquired as phase imaging data.

In an embodiment, the control unit is adapted to determine if the termination of an acquisition of a step image is caused by reaching the planned acquisition time or by reaching the step dose, wherein the control unit is further adapted to control the acquisition of subsequent step images such that subsequent step images are acquired with the same acquisition parameters as the terminated step image if the termination of the acquisition of the terminated step image was caused by reaching the step dose. Preferably the acquisition of subsequent step images is controlled such that subsequent step images are acquired with the same acquisition parameters as the first acquired step image if the termination of the acquisition of the first acquired step image was caused by reaching the step dose. In this embodiment, after the acquisition of the first step image, the determination of the applied detector dose can be omitted for the subsequent step images, since the following step images will be acquired with the same acquisition parameters, for instance, the same acquisition time and tube current, as the first step image and therefore during the acquisition of the subsequent step images the applied detector dose will correspond substantially to the step dose of the first step image. Further, in this embodiment the quality of the acquired phase imaging data can be ensured easily, since all step images are acquired using the same acquisition parameters and thus providing the same image characteristics.

In an embodiment, the step image acquisition control unit is adapted to determine a difference between the applied detector dose determined for a step image and the step dose provided for the step image, wherein the step image acquisition control unit is adapted to control the acquisition of subsequent step images further based on the difference. Preferably, the step image acquisition control unit is adapted to control the acquisition of subsequent step images further based on the difference if the applied detector dose exceeds the step dose. For instance, in this embodiment the step image acquisition control unit can be adapted to adapt the acquisition parameters for the subsequent step images such that it can be expected that the subsequent step images will be acquired with a lower applied detector dose. Moreover, the step image acquisition control unit can be adapted to control the acquisition of the subsequent step images based on the difference such that only the directly following subsequent step image is acquired using different acquisition parameters or such that all subsequent step images are acquired using different acquisition parameters.

In a preferred embodiment, the step image acquisition control unit is adapted to control the acquisition of the subsequent step images such that a determined applied detector dose is reduced for each subsequent image, respectively, if the applied detector dose exceeds the step dose and if the difference exceeds a predetermined threshold. For instance, the step image acquisition control unit can be adapted to control a tube current and the acquisition time of at least one subsequent step image such that the tube current-exposure time product is decreased and thus also the applied detector dose for this subsequent step image is decreased. Moreover, a functional link can be provided between the difference and a factor by which at least one acquisition parameter, preferably, the tube current-exposure time product, is adapted to reduce the applied detector dose. The threshold can be determined, for instance, based on the step doses. For instance, the predetermined threshold can refer to a step dose multiplied with the factor of 2, such that if the difference is greater than the step dose itself, the subsequent step images will be acquired with a reduced applied detector dose.

In an embodiment, the control module is further adapted to determine an expected target dose based on a first determined applied detector dose determined for a step image acquired first and the step image quantity, wherein the control module is adapted to further control the x-ray imaging system based on the expected target dose. Preferably, the expected target dose is determined by multiplying the first determined applied detector dose with the step image quantity. This gives a good estimate of the radiation dose that might be absorbed by the detector during the acquisition of the phase imaging data. Alternatively, the expected target dose can be calculated based on the first determined applied detector dose and the step image quantity using more advanced methods taking further assumptions about the acquisition of the subsequent phase imaging data into account, or being based on empirical values determined for previous cases with respective first determined applied detector doses and step image quantities. The control module can then be adapted, for instance, to control the x-ray imaging system by terminating the phase imaging data acquisition or to request further instructions from a user, if it is determined that the expected detector dose will exceed the target detector dose.

In an embodiment, the control module is adapted to determine a new step image quantity based on the applied detector dose of the first step image and the target detector dose when it is determined that the expected target dose is below the target detector dose, wherein the new step image quantity is determined such that the target detector dose is reached at the end of the acquisition if the subsequent step images are acquired with the same acquisition parameters as the first step image, and wherein the control module is further adapted to control the x-ray imaging unit in accordance with the newly determined step image quantity and the acquisition parameters of the first step image. Preferably, the new step image quantity is determined by dividing the target detector dose by the applied detector dose of the first step image. In this embodiment the new step image quantity will be higher than the provided step image quantity such that more than the previously planned step images can be acquired. Moreover, if the step image quantity providing unit is further adapted to provide a planned acquisition time for each step image, the control module can be adapted to determine that the expected target dose is below the target detector dose by determining that the termination of the acquisition of the first step image was caused by reaching the acquisition time, since in this case the planned step dose for the first image was not reached and it is to be expected that also for the subsequent step images the step dose will not be reached if the same acquisition parameters are used. Since in this embodiment the quantity of step images is determined such that the target detector dose is reached, the image quality of an image, like a dark-field image, reconstructed from the phase imaging data comprising the step images can be increased. Moreover, since the subsequent step images are acquired with the same acquisition parameters, the image quality of the image reconstructed from phase imaging data comprising the step images can be further increased.

In an embodiment, the control module further comprises a reconstruction unit for reconstructing an image based on the phase imaging data, wherein the reconstruction unit comprises a) a step image preparation unit for preparing all step images included in the phase imaging data acquired during phase stepping, wherein the step image preparation unit is adapted i) to normalize the step images based on the acquisition parameters used for acquiring the respective step image, and/or ii) to weight the step images based on the applied detector dose of each step image, and b) an image reconstruction unit for reconstructing the image based on the phase imaging data comprising the normalized and/or weighted step images.

Since the reconstruction unit is adapted to normalize and/or weight all step images acquired during the acquisition of the phase imaging data based on acquisition parameters or the applied step dose, respectively, different image characteristics, like different image contrasts, which are due to the controlling of the step image acquisition control unit, can be compensated. Therefore, the image reconstruction unit can reconstruct an image, for instance, a phase-contrast image, a dark field image and/or an attenuation image, with an improved image quality based on the phase imaging data comprising the normalized and/or weighted step images. Thus, in this embodiment the control module allows to accurately control a radiation dose provided to the object while at the same time providing an image reconstructed from the phase imaging data with an improved image quality.

The reconstruction unit comprises the step image preparation unit that can be adapted to normalize all step images. In particular, the step image preparation unit can be adapted to normalize each step image based on the provided acquisition parameters of the respective step image such that the normalized step images correspond to step images acquired with the same acquisition parameters if the step images are acquired using different acquisition parameters. For instance, the step image preparation unit can be adapted to normalize step images acquired with different tube currents such that the normalized step images correspond to step images acquired with the same tube current. Preferably, the step image preparation unit is adapted to normalize all step images such that the normalized step images correspond to step images that were acquired with the same tube current-exposure time product, i.e. with the same combined factor of tube current and acquisition time also commonly referred to as mAs.

Alternatively or additionally, the step image preparation unit can be adapted to weight all step images. In particular, the step image preparation unit is adapted to weight a step image by determining a weight for each step image with which the step image should be weighted during the image reconstruction based on the applied detector dose of the respective step image. Preferably, the step image preparation unit is adapted to determine a higher weight for step images for which a higher applied detector dose was determined than for step images for which a lower applied detector dose was determined. Since the step images are weighted based on the applied detector dose, it can be taken into account that step images acquired with a higher applied detector dose have a higher image quality as step images with a lower applied detector dose. The weights determined by the step image preparation unit can be determined based on a predetermined mathematical function between the image quality, in particular the noise, of a step image and the applied detector dose. For instance, it can be assumed that a quality of a step image is reduced as a root function depending on the applied detector dose, i.e. a higher applied detector dose by a factor of 2 can increase the image quality, i.e. reduce the noise, by a factor of $\sqrt{2}$. In such an embodiment, the step image preparation unit can be adapted to determine the weights for each step image based on the assumed function and based on the relation between the applied detector doses of all step images. Moreover, a function between the image quality of a step image and the applied detector dose can also be determined during a calibration of the imaging system. For instance, calibration imaging data can be acquired without the provision of an object between the radiation source and the detector, wherein the calibration imaging data is acquired for different detector doses. A function can then be estimated very accurately based on the acquired calibration imaging data. Additionally or alternatively, the weights can be determined based in predetermined weights provided for applied detector dose ranges, wherein the predetermined weights can, for instance, be determined based on a known function. Further, also the intended reconstruction algorithm can be take into account for determining the weights.

The reconstruction unit comprises the image reconstruction unit that is adapted to reconstruct the image based on the phase imaging data comprising the normalized and/or the weighted step images. In particular, the image reconstruction unit is adapted to reconstruct the image based on the i) normalized step images, ii) the normalized step images and the weights determined for the step images, or iii) on the step images and the weights determined for the step images. Since the image reconstruction unit is adapted to reconstruct the image based on the normalized and/or the weighted step images, differences in the acquisition of the step images due to the controlling of the control module have no impact on the quality of the reconstructed image. The image can be reconstructed by the image reconstruction unit based on the normalized and/or weighted step images using any known reconstruction method for reconstruction images based on phase imaging data. Preferably, the image reconstruction unit is adapted to reconstruct as image a phase-contrast image, an attenuation image and/or a dark-field image based on the phase imaging data comprising the normalized and/or weighted step images. Examples for such a reconstruction can be found in the articles "Hard-X-ray dark-field imaging using a grating interferometer" by F. Pfeiffer et.al., Nature Materials, volume 7, pages 134 to 137 (2008), and "Slit-scanning differential x-ray phase-contrast mammography: Proof-of-concept experimental studies by T. Koehler et.al., Medical Physics, volume 42, pages 1959 to 1965 (2015).

In an embodiment, the step image acquisition control unit is adapted to determine, based on the applied detector dose determined for already acquired step images, an overall detector dose and to terminate the acquisition of the phase imaging data when the overall detector dose exceeds the target detector dose. Preferably, the overall detector dose is determined by summing the applied detector doses of already acquired step images. Accordingly, the overall detector dose refers to a radiation dose that has already been provided to the object during the current acquisition of the phase imaging data. Thus, the step image acquisition control unit can ensure that the radiation dose provided to the object does not exceed the target detector dose.

In an embodiment, the step image acquisition control unit is adapted to control the step image acquisition in accordance with a robust stepping order, wherein the robust stepping order refers to acquiring the step images such that also from a quantity of step images smaller than the planned step image quantity an image, like a dark field image, can be reconstructed. For instance, if the step image quantity is provided as 10, i.e. 10 step images should be acquired, the step image acquisition control unit can be adapted to control the step image acquisition, in particular the x-ray imaging system used for acquiring the step image acquisition, such that also after the acquisition of 3 step images already an image can be reconstructed. For instance, the step image acquisition control unit can be adapted to control the step image acquisition by controlling a movement of a grating or a source point of the x-ray imaging system such that already after a lower quantity than the planned step image quantity an image can be reconstructed.

In a preferred embodiment, the step image acquisition control unit is adapted to further control movements of a grating of an x-ray imaging system used for the acquisition of the step images, wherein the controlling of the grating comprises moving the grating between the acquisition of each step image over a distance referring to a golden ratio of the grating period of the grating. The grating period of a grating generally refers to the length of periodicity of the grating. A distance referring to a golden ratio of the grating period can thus be defined by multiplying the grating period that is known of the grating with the golden ratio factor, i.e. with $g=0.5 \cdot (-1+\sqrt{5})$. In this embodiment it is further preferred that the step image quantity providing unit is adapted to provide as step image quantity a Fibonacci number, for instance, 5, 8 or 13. This is particularly advantageous if the step image acquisition control unit is adapted to control a movement of the grating based on the golden ratio of a grating period of the grating. In particular, the step position $d_j$ of a step image with number j can be selected to be $\cdot p \cdot g$, where p is the period of the grating that is stepped between the step images. The positions may be calculated modulo p in order to restrict the range of the grating movement to only one grating period. If the step quantity providing unit provided a Fibonacci number N as the quantity of step images, it can also be beneficial to provide N equidistantly placed image steps at distances $j \cdot p/N$ and to select the order of steps based on rounding $j \cdot p \cdot g$ mod p to the nearest position $i \cdot p/N$ with $i=1, \ldots N$.

In another aspect a control method for controlling an x-ray imaging system adapted to acquire phase imaging data of an object using phase stepping is presented, wherein during the phase stepping a plurality of step images, each with a different phase of an interference pattern relative to the object, are acquired with the x-ray imaging system, wherein the phase imaging data comprises the step images, wherein the method comprises the steps of a) providing a step image quantity referring to a planned quantity of step images that are to be acquired during the phase stepping for acquiring the phase imaging data, b) providing a target detector dose, wherein the target detector dose corresponds to a radiation dose absorbed by at least a part of the detector during the acquisition of the phase imaging data that should not be exceeded, c) measuring an applied detector dose indicative of a radiation dose absorbed by the at least a part of the detector during the acquisition of a step image, d) controlling the x-ray imaging system during the acquisition of each step image based on the applied detector dose, the target detector dose and the step image quantity, wherein the controlling comprises controlling acquisition parameters that each step image is acquired with.

In another aspect a computer program for controlling an x-ray imaging system is presented, wherein the computer program comprises program code means for causing the control module of claim 1 to carry out the steps of the method as defined in claim 14 when the computer program is executed by the control module.

It shall be understood that the control module of claim 1, the method of claim 14 and the computer program of claim 15 have similar and/or identical preferred embodiments, in particular, as defined in the dependent claims.

It shall be understood that a preferred embodiment of the present invention can also be any combination of the dependent claims or above embodiments with the respective independent claims.

These and other aspects of the invention will be apparent from and elucidated with reference to the embodiments described hereafter.

DETAILED DESCRIPTION OF EMBODIMENTS

Figure 1:
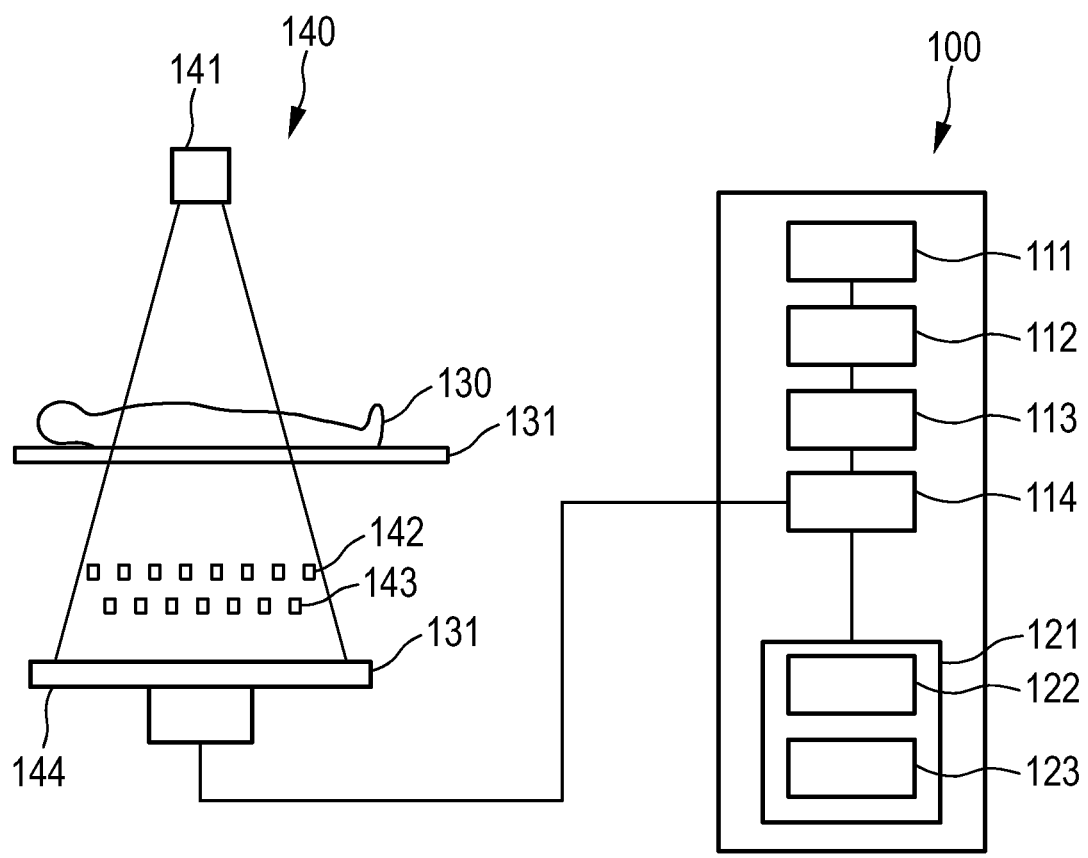
FIG. 1 shows schematically and exemplarily an embodiment of a control module for controlling an x-ray imaging system.

FIG. 1 shows schematically and exemplarily an embodiment of a control module for controlling an x-ray imaging system. In the following embodiment the control module 110 is adapted for controlling an x-ray imaging system 140 during the acquisition of phase imaging data of an object. In this embodiment, the object for which phase imaging data is acquired is a patient 130 lying on a patient table 131 such that phase imaging data can be acquired of a region of interest of the patient 130 using the x-ray imaging system 140. The x-ray imaging system 140 is adapted to acquire phase imaging data of the patient 130 by using phase stepping. In particular, the x-ray imaging system 140 comprises a radiation source 141, a detector 144 and at least two gratings 142, 143. The gratings 142, 143 are positioned such that an interference pattern of the radiation provided by the radiation source 141 to the detector 144 can be observed on the detector 144. Moreover, at least one of the gratings 142, 143 is movable with respect to the other grating 142, 143 such that an interference pattern changes its phase relative to the patient 130. For acquiring phase imaging data of the patient 130 in the following embodiment the x-ray imaging system 140 is controlled such that the gratings 142, 143 are moved relative to each other, wherein for each new position of the gratings 142, 143 a step image is acquired by the detector 144.

The control module 110 used for controlling the x-ray imaging system 140 comprises a step image quantity providing unit 111, a detector dose providing unit 112, an applied detector dose determination unit 113, a step image acquisition control unit 114 and a reconstruction unit 121.

In this embodiment the step image quantity providing unit 111 is adapted to provide a step image quantity, wherein the step image quantity refers to the quantity of step images that should be acquired during the acquisition of the phase imaging data and also to the quantity of positions of the gratings 142, 143 that should be used for acquiring the images. In this embodiment, for the following example it is assumed that the step image quantity providing unit 111 provides a step image quantity of 10. Accordingly, it is assumed that in this example it is desired to acquire 10 step images for reconstructing an image, like a phase-contrast image. A step image quantity can be provided by the step image quantity providing unit 111, for instance, based on an input of the step image quantity by a user of the system 100 or based on a general provided step image quantity stored in the system 100.

Figure 2:
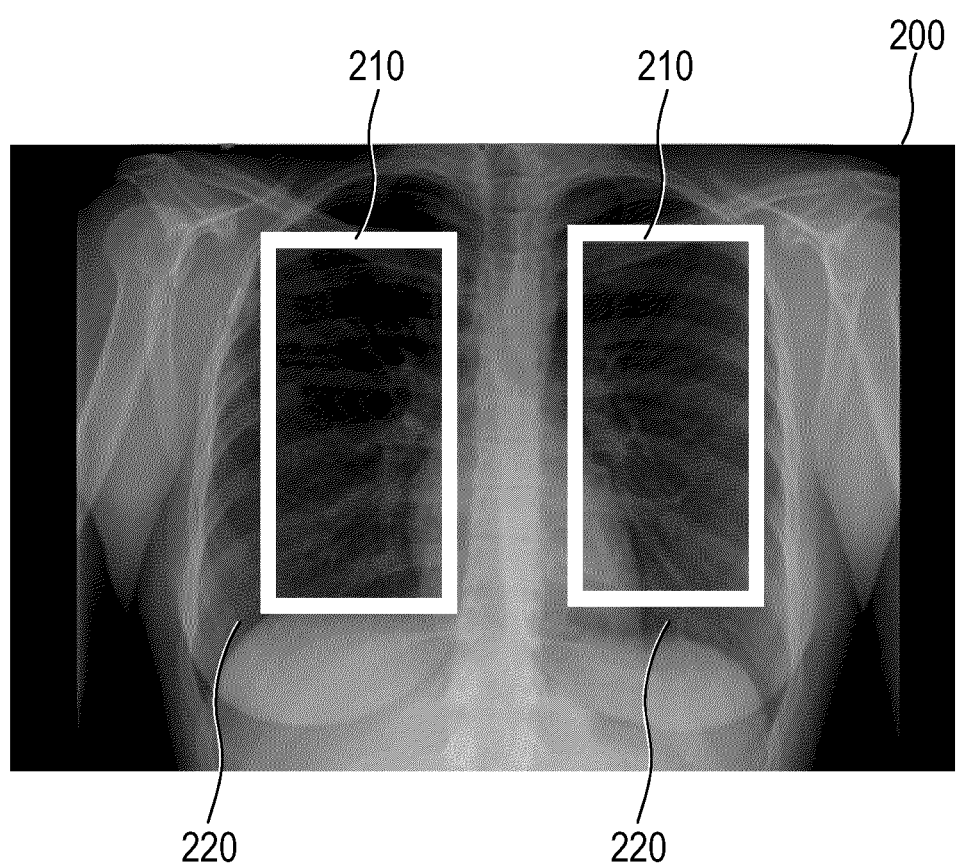
FIG. 2 shows schematically how a part of a detector for which a target detector dose is defined could be indicated.

The detector dose providing unit 112 is adapted to provide a target detector dose. In this embodiment the target detector dose refers to a radiation dose provided to the detector 144 that should not be exceeded in a certain area of the detector 144. The detector dose providing unit 112 is further adapted to provide the area of the detector 144 for which the target detector dose should not be exceeded. For instance, the detector dose providing unit 112 could provide a previously acquired and stored medical image of the region of interest of the patient 130 to a user and prompt the user to provide a part of the image for which the target detector dose should be defined. An example of such an image is given, for instance, in FIG. 2. Image 200 shown in FIG. 2 refers to an x-ray image of a lung 220 of a patient 130. In the x-ray image 200 a user has delineated a region 210 comprising two parts referring to regions in the lung 220 of the patient 130 for which the target detector dose should be defined. Based on the region 210 indicated in image 200 the detector dose providing unit 112 is adapted to determine a part of the detector 144 corresponding to the region 210 of the image 200 and thus to determine the part of the detector 144 for which the target detector dose should not be exceeded.

Further, the detector dose providing unit 112 can be adapted to provide the target detector dose based on a stored target detector dose or based on a target detector dose that is implemented by a user. In the following example it is assumed that the target detector dose refers to 2.5 mGy which is a reasonable value for lung imaging. Moreover, the detector dose providing unit 112 can be adapted to provide a step dose that, preferably, refers to a radiation dose that is received by the detector 144 in a part of the detector 144 during the acquisition of each step image. In this example the step dose is determined as a quotient of the target detector dose and the step image quantity. Accordingly, for the example provided here the step dose for each step image, i.e. for all 10 step images, refers to 0.25 mGy.

The control module 110 comprises further the applied detector dose determination unit 113 that is adapted to determine an applied detector dose. In particular, the applied detector dose determination unit 113 can be adapted to determine a radiation dose for each detector element of detector 144 based on the signals provided by the detector 144. The applied detector dose determination unit 113 can then be adapted to determine as applied detector dose an average radiation dose that has been received by the detector elements of the detector 144 in the part of the detector 144 for which the target detector dose should not be exceeded. Preferably, the applied detector dose determination unit 113 is adapted to determine the applied detector dose in real-time, i.e. to provide for each step image a current already applied detector dose. After the acquisition of the step image has been completed, the applied detector dose of a step image can be stored by the applied detector dose determination unit 113.

Moreover, the control module 110 comprises the step image acquisition control unit 114, which is adapted to control the x-ray imaging system 140 during the acquisition of each step image. In an embodiment of the system 100 the step image acquisition control unit 114 can be adapted to control the acquisition of each step image by controlling the tube current-exposure time product during the acquisition of the step image. In particular, the step image acquisition control unit 114 can be adapted to control the tube current of the radiation source 141 and the acquisition time in which a step image is acquired. A product of the tube current and the acquisition time is referred to as the tube current-exposure time product, wherein this product influences the amount of radiation provided by the radiation source 141 to the detector 144. Moreover, the step image acquisition control unit 114 is in this embodiment adapted to control the acquisition of the step images based on the applied detector dose, the target detector dose and the step image quantity. In particular, during the acquisition of each step image the step image acquisition control unit 114 compares the applied detector dose, being a current applied detector dose, with the step dose that is determined based on the target detector dose and the step image quantity. If the step image acquisition control unit 114 determines that the applied detector dose has reached the step dose, in this example, that the applied detector dose has reached 0.25 mGy, the step image acquisition control unit 114 is adapted to terminate the acquisition of the step image. Following the termination of the acquisition of the step image, the x-ray imaging system 140 is adapted to move the gratings 142, 143 with respect to each other and to start the acquisition of the next subsequent step image. Moreover, since the step dose was determined based on the target detector dose and the step image quantity and since the step image acquisition control unit 144 is adapted to terminate the acquisition of a step image if the applied detector dose equals the step dose, it can be ensured that the part of the detector 144 that should not exceed the target detector dose will not exceed the target detector dose during the acquisition of the step images.

In an alternative or additional embodiment, the step image acquisition control unit 114 is adapted to not generally terminate the acquisition of a step image if the applied detector dose reaches the step dose. In this embodiment, a predetermined threshold is provided by the step image acquisition control unit 114. The step image acquisition control unit 114 is then adapted to determine a difference between the applied detector dose of a step image and the step dose that was planned for the step image. If the difference between the applied detector dose and the step dose of the step image exceeds the predetermined threshold, the step image acquisition control unit 114 is adapted to control the subsequent step images such that the applied detector dose for the subsequent step images is reduced with respect to the previously applied detector dose. For instance, the step image acquisition control unit 114 can be adapted to control the tube current-exposure time product of subsequent step images such that the applied detector dose for the subsequent step images is decreased. Using the concrete exemplary values above, in one example the step image acquisition control unit 114 can be adapted to reduce the tube current-exposure time product for each subsequent step image by a factor of 1.5 if the step image acquisition control unit 114 has determined that during an acquisition of a step image the applied detector dose exceeded the step dose by a factor of 2, i.e. that the difference between the applied detector dose and the step dose corresponds to at least 0.25 mGy.

In a further alternative or additional embodiment, the detector dose providing unit 112 is further adapted to provide a planned acquisition time, and the step image acquisition control unit 114 is adapted to control the acquisition of a first step image such that the acquisition is terminated either when the planned acquisition time is reached or when the applied detector dose reaches the step dose of the step image during the acquisition of the step image. In this embodiment the step image acquisition control unit 114 is further adapted to determine whether the acquisition of the step image was terminated due to a) reaching the step dose or b) reaching the planned acquisition time.

If the acquisition was terminated due to reaching the step dose, the step image acquisition control unit 114 is adapted to control the acquisition of the subsequent step images such that they are acquired with the same acquisition parameters, in particular, with the same tube current-exposure time product, as the first step image. In this case the further determination of the applied detector dose can be omitted, since it can be expected that the subsequent step images will be acquired with the same applied step dose as the first step image and thus the target detector dose will be reached but not exceeded if the step dose is provided as the quotient of the target detector dose and the step image quantity.

If the acquisition was terminated due to reaching the planned acquisition time, the step image acquisition control unit 114 is adapted to determine that an expected target dose is smaller than the target detector dose if the step dose is provided as quotient of the target detector dose and the step image quantity. In this case the step image acquisition control unit 114 is further adapted to determine a new step image quantity based on the applied detector dose of the first step image and the target detector dose, for instance, by dividing the target detector dose by the applied detector dose of the first step image. The step image acquisition control unit 114 can then control the acquisition of the subsequent step images such that they are acquired with the same acquisition parameters, in particular, with the same tube current-exposure time product as the first step image, wherein step images in accordance with the new step image quantity are acquired.

Moreover, the step image acquisition control unit 114 can be adapted to determine an overall detector dose based on the already determined applied detector doses of the already acquired step images, for instance, by summing all already determined applied detector doses. When the step image acquisition control unit 114 determines that the overall detector dose is equal to or exceeds the target detector dose, the step image acquisition control unit 114 can be adapted to terminate the acquisition of the phase imaging data, i.e. to set aside the acquisition of all subsequent planned step images. Preferably, for such an embodiment the step image acquisition control unit 114 is adapted to control the acquisition of the step images such that a phase imaging data can be reconstructed also from a quantity of step images that is lower than the step quantity that was planned. For instance, it is advantageous that the step image quantity providing unit 111 provides as step image quantity a Fibonacci number, for example, 13, and that the step image acquisition control unit 114 is adapted to control the acquisition of the step images such that one of the gratings 142, 143 is moved with respect to the other grating 142, 143 by a distance corresponding to a golden ratio of the grating period of the grating 142, 143 between the acquisition of each step image.

The step image acquisition control unit 114 can be adapted to store the acquisition parameters that were used for the acquisition of each step image. Preferably, the step image acquisition control unit 114 is adapted to store the tube current-exposure time product, i.e. to store the product of the tube current and the acquisition time used for acquiring each step image. Alternatively, not the step image acquisition control unit 114 is adapted to store the acquisition parameters but another unit, like an acquisition parameter storing unit of the x-ray imaging system 140, can be adapted to store the acquisition parameters. Using the exemplary values of the above examples, the radiation intensities of the first three step images could correspond, for instance, to 100 mAs, 150 mAs and 200 mAs.

In this embodiment, the control module 111 further comprises the reconstruction unit 121 for reconstructing an image based on the phase imaging data comprising the step images acquired. The reconstruction unit 121 can comprises a step image preparation unit 122 and an image reconstruction unit 123. The step image preparation unit 122 can be adapted to normalize all acquired step images included in the phase imaging data based on the provided acquisition parameters if the step images are acquired using different acquisition parameters. In this example, the step image preparation unit 122 can be adapted to normalize each step image by dividing all image values of a respective step image by the corresponding acquisition parameter, for instance, the tube current-exposure time product. Using the exemplary values above, the step image preparation unit 122 can be adapted to divide all image values of a first step image by 100, all image values of a second step image by 150 and all image values of a third step image by 200. Moreover, the step image preparation unit 122 can further be adapted to weight the step images based on the applied detector doses. In this embodiment, the step image preparation unit 122 is adapted to determine a weight for each step image, wherein the step image is weighted with the determined weight during the reconstruction. The weight for each step image can be determined based on a predetermined function between the image quality, in particular the noise, of a step image and the applied detector dose of the step image. The weights are then determined such that they compensate for the quality differences between the step images, for instance, for step images with a higher image quality a higher weight is determined than for step images with a lower image quality. Thus, in the resulting phase imaging data comprising the normalized and weighted step images the differences during the acquisition of the step images are compensated for due to the normalization and weighting.

The image reconstruction unit 123 is then adapted to reconstruct an image based on the phase imaging data comprising the normalized step images and the weights for the step images, i.e. based on the normalized and weighted step images, according to known reconstruction algorithms. For instance, the image reconstruction unit 123 can be adapted to reconstruct a phase-contrast, a dark-field and/or an attenuation image based on the phase imaging data comprising the normalized and weighted step images.

Figure 3:
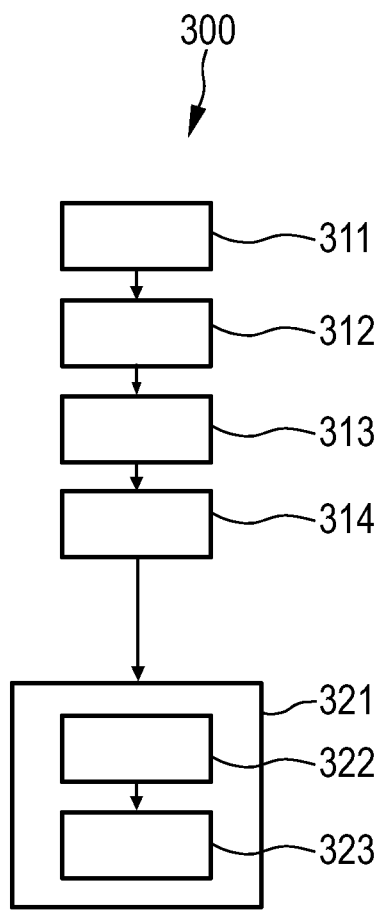
FIG. 3 shows a flowchart exemplarily illustrating an embodiment of a method for controlling an x-ray imaging system.

In the following, an embodiment of a method 300 for controlling an x-ray imaging system 140 during the acquisition of a phase imaging data of an object, being in this example a patient 130, will be described with reference to a flowchart shown in FIG. 3. The controlling method 300 comprises a first step 311 of providing a step image quantity referring to the planned quantity of step images that should be acquired during the phase stepping for acquiring the phase imaging data. In a second step 312, a target detector dose is provided, for instance, based on a part of the detector indicated by a user in an image of the patient 130, wherein the target detector dose should not be exceeded in the indicated part of the detector during the acquisition of the phase imaging data. In a third step 312, an applied detector dose is determined during the acquisition of each step image, wherein the applied detector dose preferably refers to the radiation dose received by the detector 144 during the acquisition of the step image. In the last step 314 of the controlling method 310, the x-ray imaging system 140 is controlled during the acquisition of each step image based on the applied detector dose, the target detector dose and the step image quantity. The controlling comprises the controlling of acquisition parameters used for acquiring each step image, for instance, the controlling of a tube current-exposure time product by controlling a tube current and an acquisition time used for acquiring a step image.

Optionally the method 300 further comprises a reconstruction method 321 comprising a first step 322, in which all step images acquired during the acquisition of the phase imaging data are i) normalized based on the provided acquisition parameters, for instance, based on the tube current-exposure time product, and/or ii) weighted based on the applied detector dose for each step image, such that differences during the acquisition of the step images can be compensated. Further, reconstruction method 321 comprises a step 323, in which an image is reconstructed based on the phase imaging data comprising the normalized and/or weighted images.

For optimal image quality in x-ray radiography and fluoroscopy it is advantageous to apply a predetermined optimal radiation dose to an object to be imaged, for instance, a patient. An excessive radiation dose can be harmful for the patient, whereas if the applied radiation dose is too low, the acquired image can suffer from high image noise. Therefore, to provide a sufficient image quality the application of an optimal radiation dose is advantageous. To ensure in conventional radiography, i.e. x-ray imaging, that a predetermined optimal radiation dose is provided, it is standard to use an AEC that automatically switches a radiation source off during an image acquisition once a certain radiation dose is reached on the detector. A typical radiation dose that should not be exceeded in the lung area is, for instance, 2.5 mGy.

X-ray dark-field and phase-contrast radiography, i.e. x-ray phase imaging, requires a sequence of images, for instance, 5 to 10 images, that are acquired, for instance, with an x-ray imaging system adapted as a grating interferometer. During the acquisition of phase imaging data, one of the gratings provided in the x-ray imaging system used for acquiring the phase imaging data is moved relative to the other provided gratings to obtain a stepping curve, i.e. a plurality of step images, of a phase stepping method. The acquired step images can then be used for extracting a transmission signal, a phase-contrast signal and a dark-field signal, i.e. an image, like an attenuation, a phase-contrast and a dark-field image, can be reconstructed based on the sequence of step images.

Currently, x-ray phase imaging is performed by providing predetermined tube current-exposure time product values, i.e. a value acquired by multiplying a tube current with an acquisition time, for the acquisition of each of the step images of the stepping curve. However, in clinical applications it is very challenging to estimate the radiation dose received by the detector based on a provided tube current-exposure time product and the radiation dose received by the detector based on the predetermined radiation intensities is not accurately predictable. Therefore, the invention presented here provides a system and a method for an AEC for full x-ray phase-contrast and dark-field imaging, i.e. phase imaging.

In this invention it is proposed, for instance, that a target detector dose for a part of the detector corresponding to an area where the lung or any other target organ is located clinically is defined, for instance, as 2.5 mGy. Subsequently, a quantity of steps in the stepping curve, i.e. a step image quantity, is defined, for instance, as 10. An average step dose is then preferably calculated as a ratio of the target detector dose and the step image quantity, for instance, as 0.25 mGy. This step dose can then be used to acquire all the step images during the phase imaging data acquisition. During the phase imaging data acquisition, the tube current-exposure time product applied during each step image acquisition to achieve the step dose is recorded and after image acquisition all the step images are scaled, i.e. normalized, with the intensities that were used to acquire the step image. For instance, if the intensities that were employed for the first, second and third step images are 100 mAs, 150 mAs and 200 mAs, respectively, then all image pixel values, i.e. image values, are normalized by, for instance, dividing the image values by 100, 150 and 200 for the first, second and third images, respectively. Moreover, weights can be provided for each step images based on recorded step dose for taking into account different image qualities, in particular, noise levels, of the step images. Based on these corrected, i.e. normalized, images and the weights an image, like a phase-contrast image, can be reconstructed using conventional processing methods. Such an approach makes an AEC for x-ray phase-contrast and dark-field imaging, i.e. phase imaging, possible and helps to obtain a better image quality.

In an embodiment of the above explained invention it can be advantageous to define a region of interest on the detector, i.e. a part of the detector for which the target detector dose and/or the applied detector dose will be evaluated. This can, for instance, be done by placing regions of interest where the target organ is expected to be located on the detector. Alternatively, the whole detector area can be defined as region of interest, i.e. as part of the detector.

For the chosen target area, i.e. part of the detector, for image acquisition a target detector dose, for instance, 2.5 mGy, is defined and the quantity of steps, i.e. the step image quantity, for instance, 10, is provided. A step dose can then be given, for instance, as the target detector dose divided by the step image quantity, for instance 2.5 mGy/10=0.25 mGy. This step dose can then be used for the acquisition of the stepping curve, i.e. for the acquisition of each step image, while the tube current-exposure time product settings that were used to achieve this step dose are recorded. Finally, the step images can be normalized by the tube current-exposure time product used for acquiring the respective step image. The scaled images, i.e. normalized images, can be used for conventional x-ray phase-contrast and dark-field image reconstruction together with weights determined for each step image.

Further, it is proposed that an AEC for dark-field and phase-contrast imaging, i.e. phase imaging, is based on, for instance, choosing a tube current-exposure time product setting for a patient, comprising a tube current-exposure time product for each step image that the step image should be acquired with, and entering the tube current-exposure time product settings into an x-ray imaging system used for phase imaging. This tube current-exposure time product setting is then used for the acquisition of the stepping curve, i.e. for the acquisition of the step images. In a case in which an applied detector dose determined from an average radiation dose provided to each pixel, i.e. detector element, of the region of interest of the detector for one step image exceeds the calculated step dose, for instance, 0.25 mGy, by, for instance, a factor of 2, the tube current-exposure time product setting is automatically reduced by a factor of, for instance, 1.5, for the subsequent step image acquisition. In a case in which an overall detector dose, i.e. a radiation dose received by the detector during all already acquired step images, reaches the target detector dose, for instance, 2.5 mGy, the phase imaging data acquisition is terminated. Also in this embodiment the radiation intensities used for imaging the step images are recorded and subsequently used to scale, i.e. normalize, the images. Thus, corrected images, i.e. normalized images, can be directly used for further processing.

In order to be well prepared for a terminated acquisition, it is desired to perform the acquisition using a robust stepping order, i.e. an acquisition that allows for a proper phase retrieval, i.e. reconstruction of, for instance, a phase-contrast image, from any quantity of step images between 3 and 10. In a robust stepping order, a grating provided by the x-ray imaging system may be moved by a multiple of g·p between two subsequent step images, wherein p refers to a grating period of the grating and g refers to the golden ratio. Especially advantageous stepping sequences for a grating can be generated if the step image quantity refers to a Fibonacci number, for instance, 5, 8, 13, and by using a proper rounding of the stepping scheme by increments of g·p to equally distribute positions with n steps, i.e. respective step image quantities.

In the above described embodiment the acquisition parameters, in particular, the tube current-exposure time product, will fluctuate, i.e. will be different for each acquired step image. These fluctuations can be eliminating with a re-normalization and weighting procedure.

Alternatively, an embodiment is proposed in the following in which an AEC is only used for the first step image acquisition. For instance, in a fluoroscopy mode the acquisition time, i.e. the exposure window, is limited. For example, the exposure window can have a maximum duration of 30 ms. If the patient is slim enough, the AEC of the first step image will result in an exposure time lower than the maximum exposure window. If the patient is not slim enough, the AEC will not terminate the exposure but it will be terminated by the maximum exposure window. In this case the target exposure, i.e. target detector dose (in μGy), will not be reached during the acquisition of the phase imaging data.

It is proposed that in the first case the target quantity of shots, i.e. the step image quantity, for instance, 10, is used and all step images are taken with the tube current-exposure time product from the first shot, i.e. step image. So the use of the AEC can be omitted in the successive exposures.

In the second case it is proposed that the histogram of the first step image is evaluated and the data converted into a dose to determine the applied step dose of the first step image. Then a new step image quantity is calculated by dividing the target detector dose, for instance, 2.5 mGy by the applied step dose of the first image and the subsequent step images are acquired with the same acquisition parameters as the first step image until the new step image quantity is reached.

In both cases, the acquisition parameters, in particular the tube current-exposure time product, for each shot, i.e. step image, will not fluctuate. This method of deriving the quantity of step images from the histogram of the first exposure can also be applied to the two first embodiments described above.

Although in the above embodiments the object to be imaged was a patient in a medical environment, in other embodiments the object to be imaged can also be an animal or an inanimate object like a suitcase. Moreover, the invention cannot only be provided for a medical environment, but can also be provided in the context of other applications like industrial applications or security applications.

Although in the above embodiments the x-ray imaging unit was adapted to move the gratings with respect to each other, in other embodiments the x-ray imaging unit can be adapted to provide electromagnetic phase stepping, i.e. to move a source spot of the radiation source with respect to the gratings.

Although in the above embodiment the part of the detector for which the target detector dose was defined was indicated by a user based on an image of a region of interest, in other embodiments the part of the detector can be automatically determined by the target detector dose, for instance, based on a known position of the patient relative to the detector or a standard position of the patient relative to the detector.

Although in the above embodiment the reconstruction unit was part of the controlling unit, in other embodiments the reconstruction unit can be omitted or can be a separate unit provided, for instance, on a different computing system.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the controlling of the x-ray imaging system or the reconstruction of the image based on the phase imaging data performed by one or several units or devices can be performed by any other number of units or devices. For instance, these procedures can be carried out by a single device. These procedures and/or the control of the system for acquiring a phase imaging data can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a control module for controlling an x-ray system during the acquisition of step images for phase imaging. The control module comprises a step image quantity providing unit for providing a step image quantity, a detector dose providing unit for providing a target detector dose, an applied detector dose determination unit for determining an applied detector dose absorbed by a part of the detector during the acquisition of a step image, and a step image acquisition control unit for controlling the x-ray imaging system during the acquisition of each step image based on the applied detector dose, the target detector dose and the step image quantity. The control module allows to control the x-ray imaging system such that the target detector dose is not exceeded while at the same time ensuring a sufficient quality of the step images.

The invention claimed is:

1. A control module for controlling an x-ray imaging system, comprising:
a memory that stores a plurality of instructions; and
processor circuitry that couples to the memory and is configured to execute the plurality of instructions for controlling an x-ray imaging system during the acquisition of phase imaging data of an object using phase stepping, wherein during the phase stepping a plurality of step images, each with a different phase of an interference pattern relative to the object, is acquired by the x-ray imaging system, wherein the phase imaging data comprises the step images, and wherein the processor circuitry is configured to:
provide a step image quantity referring to a planned quantity of the step images that are planned to be acquired during the phase stepping for acquiring the phase imaging data;
provide a target detector dose, wherein the target detector dose corresponds to a radiation dose absorbed by at least a part of a detector during the acquisition of the phase imaging data that should not be exceeded;
determine an applied detector dose indicative of a radiation dose absorbed by at least the part of the detector during the acquisition of a step image; and
control the x-ray imaging system during the acquisition of each step image based on the applied detector dose, the target detector dose and the step image quantity, wherein the controlling comprises controlling acquisition parameters that each step image is acquired with.

2. The control module according to claim 1, wherein the processor circuitry is configured to further provide a step dose for each step image, wherein the step dose is indicative of a radiation dose that is planned to be absorbed by at least the part of the detector during the acquisition of the respective step image, and to control the acquisition of each step image further based on the step dose.

3. The control module according to claim 2, wherein the processor circuitry is configured to provide the step dose based on the step image quantity and the target detector dose.

4. The control module according to claim 2, wherein the processor circuitry is configured to control the acquisition of a step image such that the acquisition is terminated when the applied detector dose reaches the step dose of the step image during the acquisition of the step image.

5. The control module according to claim 4, wherein the processor circuitry is configured to provide a planned acquisition time referring to a time that should not be exceeded by the acquisition of a step image, and to control the acquisition of the step images such that the acquisition is terminated either when the planned acquisition time is reached or the applied detector dose reaches the step dose of the step image during the acquisition of the step image.

6. The control module according to claim 5, wherein the processor circuitry is configured to determine if the termination of an acquisition of a step image is caused by reaching the planned acquisition time or by reaching the step dose, wherein the processor circuitry is further configured to control the acquisition of subsequent step images such that subsequent step images are acquired with the same acquisition parameters as the terminated image if the termination of the acquisition of the terminated step image was caused by reaching the step dose.

7. The control module according to claim 2, wherein the processor circuitry is configured to determine a difference between the applied detector dose determined for a step image and the step dose provided for the step image, wherein the processor circuitry is configured to control the acquisition of subsequent step images further based on the difference.

8. The control module according to claim 7, wherein the processor circuitry is configured to control the acquisition of the subsequent step images such that a determined applied detector dose is reduced for each subsequent image, respectively, if the applied detector dose exceeds the step dose and if the difference exceeds a predetermined threshold.

9. The control module according to claim 1, wherein the processor circuitry is configured to determine an expected target dose based on a first determined applied detector dose determined for a step image acquired first and the step image quantity, wherein the processor circuitry is configured to control the x-ray imaging system based on the expected target dose.

10. The control module according to claim 9, wherein the processor circuitry is configured to determine a new step image quantity based on the applied detector dose of the first step image and the target detector dose if the expected target dose is below the target detector dose, wherein the new step image quantity is determined such that the target detector dose is reached at the end of the acquisition if the subsequent step images are acquired with the same acquisition parameters as the first step image, and wherein the processor circuitry is configured to control the x-ray imaging unit in accordance with the new step image quantity and the acquisition parameters of the first step image.

11. The control module according to claim 1, wherein the processor circuitry is configured to:
prepare all step images included in the phase imaging data acquired during phase stepping, wherein the processor circuitry is configured to normalize the step images based on the acquisition parameters used for acquiring the respective step image, and/or weight the step images based on the applied detector dose of each step image.

12. The control module according to claim 1, wherein the processor circuitry is configured to determine, based on the applied detector dose determined for already acquired step images, an overall detector dose and terminate the acquisition of the phase imaging data when the overall detector dose exceeds the target detector dose.

13. The control module according to claim 1, wherein the processor circuitry is configured to control the step image acquisition in accordance with a robust stepping order, wherein the robust stepping order refers to acquiring the step images such that also from a quantity of step images smaller than the planned step image quantity an image can be reconstructed based on the phase imaging data comprising the step images.

14. A control method, comprising for controlling an x-ray imaging system during the acquisition of a phase imaging data of an object using phase stepping, wherein during the phase stepping a plurality of step images, each with a different phase of an interference pattern relative to the object, is acquired with an x-ray imaging system, wherein the phase imaging data comprises the step images, wherein the control method comprises the steps of:
controlling an x-ray imaging system during the acquisition of a phase imaging data of an object using phase stepping, wherein during the phase stepping a plurality of step images, each with a different phase of an interference pattern relative to the object, is acquired by the x-ray imaging system, wherein the phase imaging data comprises the step images;
providing a step image quantity referring to a planned quantity of the step images that are planned to be acquired during the phase stepping for acquiring the phase imaging data;
providing a target detector dose, wherein the target detector dose corresponds to a radiation dose absorbed by at least a part of the detector during the acquisition of the phase imaging data that should not be exceeded;
determining an applied detector dose indicative of a radiation dose absorbed by at least the part of the detector during the acquisition of a step image; and
controlling the x-ray imaging system during the acquisition of each step image based on the applied detector dose, the target detector dose and the step image quantity, wherein the controlling comprises controlling acquisition parameters that each step image is acquired with.

15. A non-transitory computer-readable medium for storing executable instructions that, when executed, cause the method of claim 14 to be performed.

* * * * *